United States Patent [19]
Marcus et al.

[11] Patent Number: 5,852,020
[45] Date of Patent: Dec. 22, 1998

[54] NEFAZODONE: USE IN TREATING POST TRAUMATIC STRESS DISORDER

[75] Inventors: Ronald N. Marcus; Brenda Martini, both of Hamden, Conn.

[73] Assignee: Bristol-Myers Squibb Company, Princeton, N.J.

[21] Appl. No.: 904,011

[22] Filed: Jul. 31, 1997

Related U.S. Application Data

[60] Provisional application No. 60/031,914, Nov. 22, 1996.
[51] Int. Cl.$^6$ .................................................. A61K 31/449
[52] U.S. Cl. ........................................... 514/252; 514/359
[58] Field of Search ...................................... 514/252, 359

[56] References Cited

U.S. PATENT DOCUMENTS

| | | | |
|---|---|---|---|
| 4,338,317 | 7/1982 | Temple et al. ........................... | 424/250 |
| 5,116,852 | 5/1992 | Gammans ................................ | 514/359 |
| 5,644,057 | 7/1997 | Yuan et al. .............................. | 544/280 |

OTHER PUBLICATIONS

USP Dictionary of USAN and International Drug Names, 1995, p. 459.

Taylor, et al., "Nefazodone Hydrochloride," *Drugs of the Future,* 1987 12(8), pp. 758–759.

Eison, et al., "Nefazodone: Preclinical Pharamacology of a New Antidepressant" *Psychopharmacology Bulletin,* 26(3) 1990: pp. 311,315.

Frank, et al., "A Randomized Clinical Trial of Phenelzine and Imipramine for PTSD," *Am. J. Psychiatry,* 145, 1988: pp. 1289–1291.

Birkhimer, et al., "PTSD: Characteristics and Pharmacological Response in the Veteran Population," *Comprehensive Psychiatry,* 1985, 26/3, pp. 304–310.

Reist, et al., "A Controlled Trial of Desipramine in 18 Men with PTSD," *Am. J. Psychiatry,* 1989, 146:4, pp. 513–516.

Davidson, et al., "Treatment of PTSD with Amytriptyline and Placebo," *Arch. Gen. Psychiatry* 1990, 47, pp. 259–266.

Bremner, et al., "Chronic PTSD in Vietnam Combat Veterans: Course of Illness and Substance Abuse," *Am. J. Psychiatry,* 1996, 153, pp. 369–375.

Davidson, et al., "Predicting Response to Amitriptyline in PTSD," *Am. J. Psychiatry,* 1993, 150, pp. 1024–1029.

Marmar, et al., "Open Trail of Fluvoxamine Treatment for Combat–Related PTSD," *J. Clin. Psychiatry,* 1996, 57, Supl. 8, pp. 66–72.

Zajecka, U.S Psychiatric & Mental Health Congress, pp. 1–3 Nov. 14–17 1996.

Friedman et al, PTSD Research Quarterly, Summer 1990.

*Primary Examiner*—James H. Reamer
*Attorney, Agent, or Firm*—Richard P. Ryan

[57] ABSTRACT

Nefazodone and its pharmaceutically acceptable salts are useful in alleviation of post traumatic stress disorder.

7 Claims, No Drawings

NEFAZODONE: USE IN TREATING POST TRAUMATIC STRESS DISORDER

FIELD OF INVENTION

This application claims benefit of provisional application 60/031,914 filed Nov. 22, 1996.

This invention relates to the treatment of post traumatic stress disorder (PTSD) with nefazodone.

BACKGROUND OF THE INVENTION

This invention is concerned with a drug bio-affecting body-treating process which employs the compound 2-[3-[4-(3-chlorophenyl)-1-piperazinyl]propyl]-5-ethyl-2,4-dihydro-4-(2-phenoxyethyl)-3H-1,2,4-triazol-3-one or a pharmaceutically acceptable acid addition salt thereof.

This compound has the following structural formula (I)

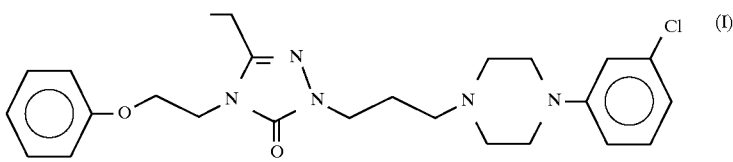

and is known as nefazodone. The hydrochloride salt has been referred to in the literature as MJ 13754-1 and as BMY 13754, as well as nefazodone hydrochloride, which is the United States Adopted Name (USAN); refer to "USP Dictionary of USAN and International Drug Names," 1995, p. 459.

Synthesis of nefazodone and close analogs and disclosure of its pharmacology are described in the following patents and publications.

1. Temple, et al, U.S. Pat. No. 4,338,317 issued Jul. 6, 1982.
2. Gammans, U.S. Pat. No. 5,116,852, issued May 26, 1992.
3. D. P. Taylor, et al, "Nefazodone Hydrochloride," Drugs of the Future, 12(8) pp. 758–759 (1987).
4. A. Eison, et al, "Nefazodone: Preclinical Pharmacology of a New Antidepressant," Psychopharmacology Bulletin, 26(3) pp. 311,315 (1990).

Clinical studies of nefazodone have indicated its usefulness as an antidepressant agent and nefazodone hydrochloride has been approved by the U.S. Food and Drug Administration for use in treating depressed patients. Nefazodone also appears to have sleep normalizing properties in a human population. This contrasts with effects on sleep seen for other antidepressant drugs.

The method of the present invention can be distinguished from the above prior art in that it is directed to a distinct patient population characterized by a disease state different from that related to depression disclosed in this prior art.

Post traumatic stress disorder (PTSD) is defined by DSM-IV (Diagnostic and Statistical Manual, 4th edition) as an anxiety disorder which develops following exposure to an extremely traumatic event. The diagnosis of PTSD is made when the following core symptoms follow exposure to the trauma: the traumatic event is persistently re-experienced (via intrusive thoughts, dreams, flashbacks, or internal and external cues); there is persistent avoidance of evidence associated with the trauma or generalized psychological numbing and isolation; and there is widespread physiologic arousal which was not present prior to the trauma.

Psychopharmacologic treatment of PTSD is primarily symptomatic and has encompassed agents from all categories of centrally-acting drugs. The outcome of pharmacotherapy for PTSD patients, unfortunately, is generally inadequate. While antidepressant therapy is the most widely utilized treatment for PTSD, there are currently no drugs approved for this indication. The availability of controlled clinical trial data in the literature for the treatment of PTSD is limited. Those studies that have been published suggest a modest improvement in PTSD symptomatology following treatment with either tricyclic antidepressants (imipramine, amitriptyline, desipramine), monoamine oxidase inhibitors (MAOs), pheneizine or clonidine. While these treatment options are often used, they are not standardly accepted pharmacotherapy for PTSD and carry with them risks of cardiovascular side effects, drug interactions, and anticholinergic and peripheral side effects.

The following representative references are typical in reporting some symptom reductions in PTSD patients following medication with various centrally-acting agents, particularly antidepressants and antipsychotics.

a. Frank, et al., "A Randomized Clinical Trial of Phenelzine and Imipramine for PTSD," Am. J. Psychiatry, 1988, 145:1289–1291.
b. Birkhimer, et al., "PTSD: Characteristics and Pharmacological Response in the Veteran Population," Comprehensive Psychiatry, 1985; 26/3, 304–310.
c. Reist, et al., "A Controlled Trial of Desipramine in 18 Men with PTSD," Am. J. Psychiatry, 1989, 146:4, 513–516.
d. Davidson, et al., "Treatment of PTSD with Amytriptyline and Placebo," Arch. Gen. Psychiatry, 1990, 47:259–266.
e. Bremner, et al., "Chronic PTSD in Vietnam Combat Veterans: Course of Illness and Substance Abuse," Am. J. Psychiatry 1996, 153:369–375.
f. Davidson, et al., "Predicting Response to Amitriptyline in PTSD," Am. J. Psychiatry, 1993, 150:1024–1029.
g. Marmar, et al., "Open Trial of Fluvoxamine Treatment for Combat-Related PTSD," J. Clin. Psychiatry, 1996, 57, Suppl. 8, 66–72.

None of these or other references suggest that nefazodone would be effective in the treatment of PTSD.

SUMMARY OF THE INVENTION

The method of the present invention is intended for the alleviation of PTSD in patients suffering from the disorder and a more complete symptom response is expected. The process essentially involves administration of nefazodone, or a pharmaceutically acceptable acid addition salt thereof, to one in need of such treatment. For use in the instant process, oral administration of nefazodone hydrochloride ranges from about 100 to 600 mg per day. Administration of about 300 to 600 mg per day in divided doses is anticipated as being the preferred dosage regimen. While various centrally-acting drug treatments have been employed for symptomatic relief in PTSD patients, it is likely that nefazodone possesses important clinical distinctions from previous treatments because of its dual effects on serotonergic transmission. Nefazodone modulates serotonin receptors not only by selective blockade of 5-HT$_2$ receptors but by blocking 5-HT reuptake as well. It is believed that this novel pharmacology of nefazodone will result in unique therapeutic activity in treatment of PTSD.

DETAILED DESCRIPTION OF THE INVENTION

Post traumatic stress disorder follows an occurrence of a traumatic episode that would cause significant distress in almost everyone. Examples comprise incidents of violent confrontation, such as rape or assault or a serious accident. Warfare and natural disasters, particularly when a loss of companions or individuals close to the sufferer is experienced in the course of these incidents, can also be inducers of the disorder. Soon after the traumatic event the affected individual frequently feels detached or estranged from others and general responsiveness to the environment declines. Feelings of depression and lack of interpersonal interactions are other symptoms frequently experienced following the incident. More detailed diagnostic criteria are found in DMS-IV but in general PTSD sufferers may exhibit symptoms of anxiety, hostility, depression and withdrawal. This constellation of PTSD symptoms is resistant to the currently available pharmacotherapies.

From a pre-clinical viewpoint, nefazodone with its novel dual serotonergic mechanism of action can be expected to enhance serotonergic transmission in PTSD patients. This effect should ameliorate the disorder since it has been shown in animal stress testing models that serotonin agonists reverse stress responses to inescapable shock. Serotonin release is also recognized as an inhibitor of aggression and a regulator of impulse control. Such effects should relate to PTSD behavioral components such as avoidant symptoms in sexually traumatized women and/or explosive outbursts and rage in depressed war veterans. It is expected that nefazodone will be particularly useful in reducing depression, anxiety and hostility in PTSD patients.

Intrusive symptoms of PTSD such as nightmares, sleep disorders and startle reactions should also be particularly responsive to nefazodone. Nefazodone has been shown to have antianxiety and sleep-normalizing properties and has demonstrated clinical efficacy in the treatment of depressive disorders accompanied by prominent anxiety and sleep disturbance symptomatology.

It has now been clinically observed that the administration of nefazodone alleviated PTSD in diagnosed sufferers. Several pilot studies in patients meeting DSM-IV criteria for diagnosis of PTSD have been conducted. Currently, large-scale controlled studies are planned. In one pilot study patients having had no psychotropic medication for two weeks and who were free of significant cardiac or medical conditions were given a baseline evaluation. The evaluation included completion of several psychometric instruments as well as monitoring the individual's heart rate and blood pressure response while listening to an audiotaped description of the patient's traumatic experience. The study subjects were then treated with nefazodone (300 to 600 mg per day reached by individual titration) for a ten-week period and then re-evaluated using the baseline test methods. In general, considerable improvement in reduction of post traumatic stress symptomatology and in physiological response to rehearing the audio tape have been observed for patients completing the study. Several patients reported a marked improvement in the sleep disturbance component of PTSD.

Another small study involved open-label treatment of victims of a bombing incident. The majority of patients had PTSD accompanied by depression and/or generalized anxiety. All patients treated with nefazodone exhibited an excellent response. Some of the patients had initially been started on selective serotonin reuptake inhibitors, such as Prozac or Paxil, but these agents proved to be too activating for the patients.

Another uncontrolled pilot study involved a baseline measurement with several rating scales followed by a 12-week drug administration period. Nefazodone was administered initially as a 50 mg dose and then titrated individually to a maximum of 600 mg per day. Patient response was measured in terms of reduction of rating scale scores following nefazodone administration. In all the pilot studies nefazodone appeared to be well tolerated by the PTSD patients.

The method of the present invention essentially involves administration of nefazodone, or a pharmaceutically acceptable acid addition salt thereof, to a patient suffering from PTSD. Pharmaceutically acceptable acid addition salts of nefazodone and methods of pharmaceutical formulation are described in the patent of Temple, et al., U.S. Pat. No. 4,338,317, which is incorporated herein in its entirety by reference.

Administration of nefazodone hydrochloride according to the present invention may be by the parenteral, oral, or rectal routes. The oral route is preferred, however. The clinical dosage for alleviation of PTSD is expected to be 100 to 600 mg per day, generally in the 200 to 600 mg range and preferably in the range of 300 to 600 mg per day. Since the dosage should be tailored to the individual patient, the usual practice is to commence with a dose of about 50 mg administered once or twice a day and then to increase the dose every week by 50 to 100 mg at each dosage time until the desired response is observed or until the patient exhibits side effects.

We claim:

1. A method for alleviation of post traumatic stress disorder (PTSD) which comprises administering a non-toxic therapeutically effective dose of nefazodone or a pharmaceutically acceptable acid addition salt thereof to a patient in need of such treatment.

2. The method of claim 1 wherein nefazodone hydrochloride is employed and dosage is by the oral route.

3. The method of claim 1 wherein depression is a major component of the PTSD afflicting said patient.

4. The method of claim 1 wherein hostility is a major component of the PTSD afflicting said patient.

5. The method of claim 1 wherein sleep disturbance is a major component of the PTSD afflicting said patient.

6. The method of claim 2, 3, 4, or 5 wherein said patient is an adult and a daily dose of from about 300 mg to 600 mg is employed.

7. The method of claim 6 wherein said daily dose is divided and administered b.i.d.

* * * * *